(12) United States Patent
Greenberg et al.

(10) Patent No.: US 7,962,221 B2
(45) Date of Patent: Jun. 14, 2011

(54) PIXEL RE-MAPPING FOR VISUAL PROSTHESIS

(75) Inventors: Robert J. Greenberg, Los Angeles, CA (US); Richard Williamson, Saugus, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 550 days.

(21) Appl. No.: 11/493,471

(22) Filed: Jul. 25, 2006

(65) Prior Publication Data

US 2007/0027503 A1 Feb. 1, 2007

Related U.S. Application Data

(62) Division of application No. 10/355,791, filed on Jan. 31, 2003, now Pat. No. 7,574,263.

(51) Int. Cl.
*A61N 1/36* (2006.01)
(52) U.S. Cl. .......................................... 607/54; 607/53
(58) Field of Classification Search .................. 607/53, 607/54; 600/558, 383; 623/6.63
See application file for complete search history.

(56) References Cited

U.S. PATENT DOCUMENTS

| | | | |
|---|---|---|---|
| 4,628,933 A | 12/1986 | Michelson | |
| 5,109,844 A | 5/1992 | de Juan, Jr. et al. | |
| 5,159,927 A * | 11/1992 | Schmid | 607/53 |
| 5,570,142 A | 10/1996 | Lieberman | 351/160 R |
| 5,935,155 A | 8/1999 | Humayun et al. | |
| 5,944,747 A | 8/1999 | Greenberg et al. | |
| 6,400,989 B1 * | 6/2002 | Eckmiller | 607/54 |
| 6,920,358 B2 | 7/2005 | Greenberg et al. | 607/54 |
| 2002/0010496 A1 * | 1/2002 | Greenberg et al. | 607/54 |
| 2002/0037061 A1 | 3/2002 | Learned | |
| 2002/0087202 A1 | 7/2002 | Chow et al. | 607/53 |
| 2002/0193845 A1 | 12/2002 | Greenberg et al. | 607/54 |
| 2004/0176821 A1 | 9/2004 | Delbeke et al. | 607/54 |

* cited by examiner

*Primary Examiner* — Michael Kahelin
(74) *Attorney, Agent, or Firm* — Scott B. Dunbar; Alessandro Steinfl; Tomas Lendvai

(57) ABSTRACT

A method and apparatus for adjusting a visual image provided to a patient. In one embodiment, an image may be presented to the patient to obtain the patient's subjective perception of the image, and the patient may either manipulate the image to obtain a desired adjustment, or guide a clinician performing the adjustment. In another embodiment, the clinician may make objective observations of, for example, the position of an electrode array on the patient's retina, and make adjustments accordingly. The adjustment may be a spatial adjustment comprising a re-mapping performed to decreases image distortion resulting from differences in the patient's perception of stimulation of different areas of the retina. Such distortion may result from differences between the patient's perception of stimulation falling within the macula, and stimulation falling within the periphery surrounding the macula. The adjustment may also compensate for translations or rotations of the electrode array on the retina.

15 Claims, 13 Drawing Sheets

| | | | | | | | |
|---|---|---|---|---|---|---|---|
| 11 | 12 | 13 | 14 | 15 | 16 | 17 | 18 |
| 21 | 22 | 23 | 24 | 25 | 26 | 27 | 28 |
| 31 | 32 | 33 | 34 | 35 | 36 | 37 | 38 |
| 41 | 42 | 43 | 44 | 45 | 46 | 47 | 48 |
| 51 | 52 | 53 | 54 | 55 | 56 | 57 | 58 |
| 61 | 62 | 63 | 64 | 65 | 66 | 67 | 68 |
| 71 | 72 | 73 | 74 | 75 | 76 | 77 | 78 |
| 81 | 82 | 83 | 84 | 85 | 86 | 87 | 88 |

FIG. 6A

| | | | | | | | |
|---|---|---|---|---|---|---|---|
| 11 | 12 | 13 | 14 | 15 | 16 | 17 | 18 |
| 21 | 22 | 23 | 24 | 25 | 26 | 27 | 28 |
| 31 | 32 | 33 | 34 | 35 | 36 | 37 | 38 |
| 41 | 42 | 43 | 44 | 45 | 46 | 47 | 48 |
| 51 | 52 | 53 | 54 | 55 | 56 | 57 | 58 |
| 61 | 62 | 63 | 64 | 65 | 66 | 67 | 68 |
| 71 | 72 | 73 | 74 | 75 | 76 | 77 | 78 |
| 81 | 82 | 83 | 84 | 85 | 86 | 87 | 88 |

| 11 | 12 | 13 | 14 | 15 | 16 | 17 | 18 |
| 21 | 22 | 23 | 24 | 25 | 26 | 27 | 28 |
| 31 | 32 | 33 | 34 | 35 | 36 | 37 | 38 |
| 41 | 42 | 43 | 44 | 45 | 46 | 47 | 48 |
| 51 | 52 | 53 | 54 | 55 | 56 | 57 | 58 |
| 61 | 62 | 63 | 64 | 65 | 66 | 67 | 68 |
| 71 | 72 | 73 | 74 | 75 | 76 | 77 | 78 |
| 81 | 82 | 83 | 84 | 85 | 86 | 87 | 88 |

FIG. 6C

| 11 | 12 | 13 | 14 | 15 | 16 | 17 | 18 |
| 21 | 22 | 23 | 24 | 25 | 26 | 27 | 28 |
| 31 | 32 | 33 | 34 | 35 | 36 | 37 | 38 |
| 41 | 42 | 43 | 44 | 45 | 46 | 47 | 48 |
| 51 | 52 | 53 | 54 | 55 | 56 | 57 | 58 |
| 61 | 62 | 63 | 64 | 65 | 66 | 67 | 68 |
| 71 | 72 | 73 | 74 | 75 | 76 | 77 | 78 |
| 81 | 82 | 83 | 84 | 85 | 86 | 87 | 88 |

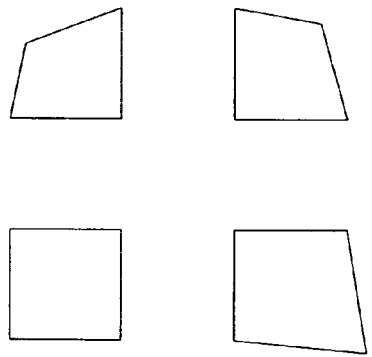
FIG. 9B
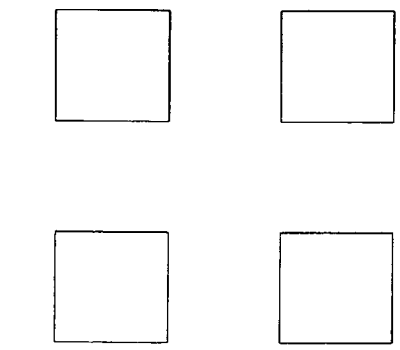
FIG. 9D
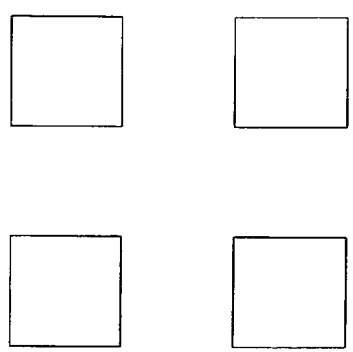
FIG. 9A
FIG. 9C

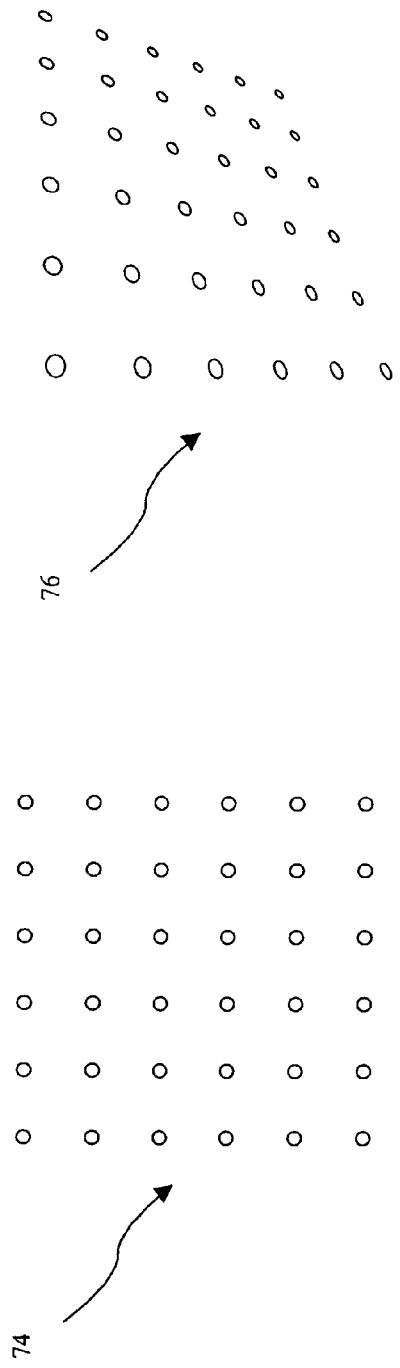
FIG. 10A
FIG. 10B
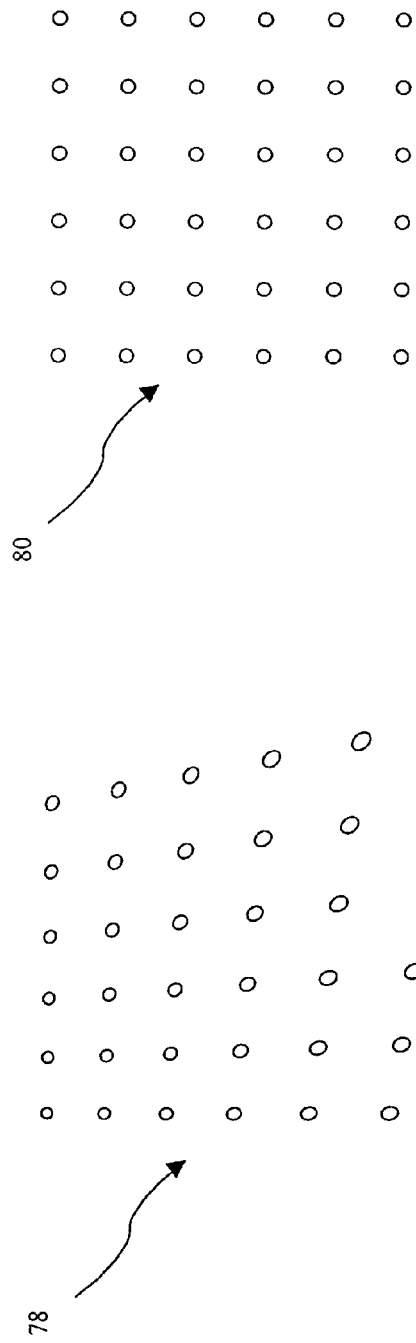
FIG. 10C
FIG. 10D

PIXEL RE-MAPPING FOR VISUAL PROSTHESIS

CROSS REFERENCE TO RELATED APPLICATION(S)

This application is a divisional application of U.S. patent application Ser. No. 10/355,791 now U.S. Pat. No. 7,574,263, filed Jan. 31, 2003.

FIELD OF THE INVENTION

The present invention is generally directed to visual, e.g., video, processing techniques, and is of particular use in conjunction with an implantable medical device, e.g., a retinal prosthesis, for reducing the distortion of images as perceived by a patient.

BACKGROUND OF THE INVENTION

Various conditions, e.g., age-related macular degeneration, retinitis pigmentosa, etc., exist which effect the functioning of photoreceptors (i.e., rods and cones) on a patient's retina and thus eliminate or severely degrade the patient's vision. To overcome these conditions, it has been proposed to directly stimulate the visual cortex or to implant a retinal prosthesis to stimulate neural pathways within a patient's retina. Stimulation of the visual cortex is described by Bindley G, Lewin W. "The sensations produced by electrical stimulation of the visual cortex," J. Physiol (London) 1968:196:479-493. Apparatus for stimulation of the retina is described in U.S. Pat. No. 4,628,933 issued to Michelson on Dec. 16, 1986 for "Method And Apparatus For Visual Prosthesis," and in U.S. Pat. No. 5,935,155 issued to Humayun et al on Aug. 10, 1999 for "Visual Prosthesis And Method Of Using Same." The '933 patent and the '155 patents are herein incorporated by reference.

The '155 patent describes an electrode array adapted to be implanted on the retina, covering the fovea. Several methods of attaching the electrode array to the retina are described in the '155 patent. As is obvious from the methods of attaching the electrode array, the placement of the electrode array is likely to be in-exact. For example, the array may be translated and/or rotated relative to an ideal position. Additionally, nerves in the retina are not uniformly spaced, particularly when comparing the retina as a whole, and the macula.

Either translation or rotation of the electrode array, relative to idea placement, may result a false perception of an object's location by a patient. Also, the perception of the size of an object associated with the stimulation may vary depending on which nerves are being stimulated. For example, stimulation of nerves within the macula may produce a different spatial perception than the same pattern of stimulation of nerves in the periphery around the macula. As a result, some objects may be perceived to be larger or smaller than they are, and the proportions of an object may be warped.

Accordingly, there is a need for methods and apparatus for adjusting the mapping of a pixilated image onto electrodes used for stimulation.

SUMMARY OF THE INVENTION

The present invention provides a method and apparatus for adjusting a visual image provided to a patient. In one embodiment, an image may be presented to the patient to obtain the patient's subjective perception of the image, and the patient may either manipulate the image to obtain a desired adjustment, or guide a clinician performing the adjustment. In another embodiment, the clinician may make objective observations of, for example, the position of an electrode array on the patient's retina, and make adjustments accordingly. The adjustment may be a spatial adjustment comprising a re-mapping performed to decreases image distortion (i.e., to address an undesirable characteristic of the image) resulting from differences in the patient's perception of stimulation of different areas of the retina. Such distortion may result from differences between the patient's perception of stimulation falling within the macula, and stimulation falling within the periphery surrounding the macula. The adjustment may also compensate for translations or rotations of the electrode array on the retina. Adjustments may also be made to aid the patient in interpreting the image, for example a black/white inversion of the image.

Known visual prostheses include a camera (or other image source), an image shaper, a pixel encoder, a carrier generator, a modulator, and a primary coil or the like as elements of an external device or devices, and further include a secondary coil, a rectifier, a demodulator, a decoder/demultiplexor, a current generator, and an electrode array or the like as implantable elements. Such visual prosthesis is described in U.S. Pat. No. 5,935,155 issued Aug. 10, 1999 for "Visual Prosthesis And Method Of Using Same," which patent is incorporated herein by reference above. In one embodiment of the present invention, an image processor is included in the external device(s), which image processor includes means for re-mapping (i.e., adjusting) the image to remove distortions in the pattern perceived by the patient. In another embodiment of the present invention, an adjustable camera is used to adjust the image. The adjustable camera may include an adjustable lens, and adjustable CCD, a processor to electronically process the video signal in the camera, or the some other means within the camera to adjust the image.

The present invention further includes methods for spatially adjusting the image to remove distortions in the image perceived by the patient. A first method comprises providing an unadjusted image to the patient. The adjustment may be performed by a clinician guided by the patient, or directly performed by the patient. The adjustment may comprise a single step of manipulation the entire unadjusted image, in which case the unadjusted image may be a scene, or may be a pattern adapted to facilitate the adjustment. In another embodiment of the present invention, the adjustment may comprise one or more steps including providing a centering feature to center the overall image, providing at least one demarcation line to adjust a boundary, and at least one feature to adjust the areas separated by the boundary.

Another method according to the present invention comprises adjustment based on clinician observations of objective indications indicative of distortions, which observations may include observations of the topology of the patient's eye made by a clinician, by observations of the final placement of the electrode array, by past observations (i.e., experience) of the clinician, or by any other observation not requiring feedback from the patient.

It is intended that any visual prosthesis which includes apparatus or methods to remove distortions from an image presented to a patient, come within the scope of the present invention.

BRIEF DESCRIPTION OF THE DRAWINGS

FIG. 6A shows an original image;

FIG. 6B shows a distorted version image of FIG. 6A;

FIG. 6C depicts an intermediate version of the image of FIG. 6A, which intermediate version has been processed by an image processor in anticipation of the distortion;

FIG. 6D shows a corrected version of the image of FIG. 6A as perceived by the patient, which corrected image is processed by the image processor in anticipation of distortion;

FIG. 9A shows a perceived image which has been centered as depicted in FIG. 9B, but shows a distortion of a first line and of a second line;

FIG. 9B depicts the image of FIG. 9A after adjusting the first line to be perceived as horizontal, and the second line as being perceived as vertical;

FIG. 10A shows an original image comprising four squares which coincide with four quadrants of an image which has been centered, and which has been adjusted to make the first line substantially horizontal and the second line substantially vertical;

FIG. 10B depicts an example of how the image of FIG. 10A might be perceived by a patient (the image remains centered and the side corresponding to the first line and the second line remain substantially horizontal and vertical);

FIG. 10C depicts an adjusted image generated by the image processor (i.e., at the output of the image processor) to compensate for the distortion perceived by the patient in the image of FIG. 10B;

FIG. 10D depicts the image perceived by the patient from stimulation based on the adjusted image of FIG. 10C;

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

The present invention is directed to reducing visual image distortion, and is of particular use in conjunction with a visual prosthesis, e.g., a retinal prosthesis, for reducing the distortion perceived by a patient. Various conditions, e.g., age-related macular degeneration, retinitis pigmentosa, etc., exist which effect the functioning of photoreceptors (i.e., rods and cones) on a patient's retina and thus eliminate or severely degrade the patient's vision. To overcome these conditions, various apparatus have been proposed to provide vision to such patients. There are three main structures that have been described in the art. In a first structure (referred to herein as a Bindley type apparatus), an input from a video camera is used to stimulate discrete points on the patient's cerebral cortex. In a second structure (referred to herein as a Humayun type apparatus), an input from a video camera is used to stimulate discrete points on a patient's retina. In a third structure (referred to herein as a Michelson type apparatus) optical sensors are supplied in a one-to-one relationship to stimulate discrete points on a patient's retina. Each of these structures potentially suffer from image distortion due to misplacement of the electrode array (either translational or rotational), and the stimulation of nerves within the macula may produce a different spatial perception than the same pattern of stimulation of nerves in the periphery around the macula. As a result, some objects may be perceived to be larger or smaller than they are, and the proportions of an object may be warped. The present invention address the aforementioned issues by adjusting the image based on the patients perception, to remove such translations, rotations, and distortions.

Figure 1:
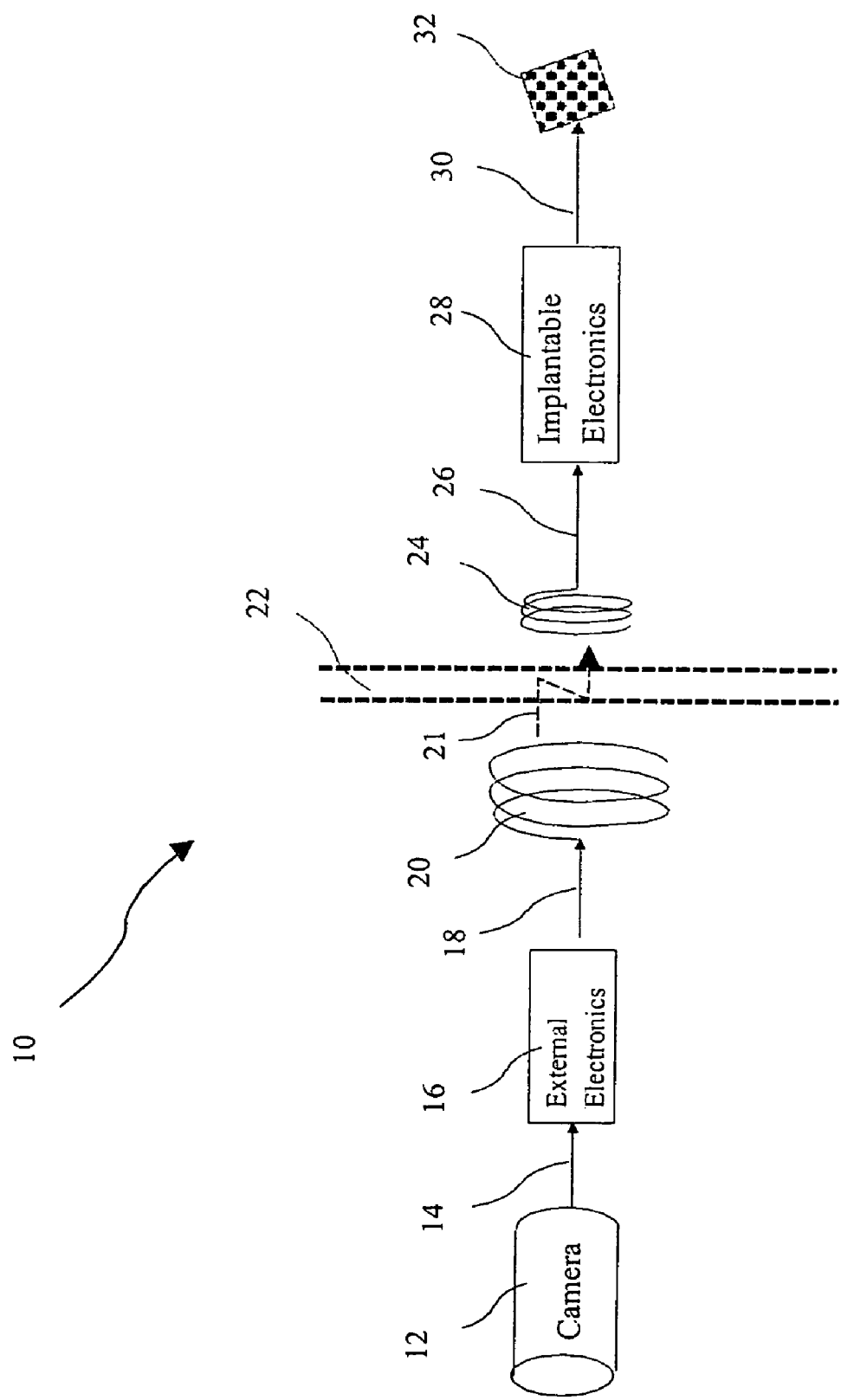
FIG. 1 shows a block diagram of a visual prosthesis.

An example of a retinal prosthesis 10 is shown in FIG. 1. The retinal prosthesis 10 includes a camera 12, for example a Charge Coupled Device (CCD), or other image source, which generates a video signal 14. Other image sources may include a television composite signal or computer output. The video signal 14 is received by external electronics 16, which generates a Radio Frequency (RF) modulated signal 18. The RF modulated signal 18 is then transmitted via primary coil 20 as an RF transmission 21 through skin 22. A secondary coil 24 receives the RF transmission 21 and provides a received signal 26 to implantable electronics 28. The implantable electronics 28 generates a stimulation current signal 30, which is provided to an electrode array 32. The electrode array 32 stimulates the retinal cells to produce phosphenes in a pattern to create a sensation of vision. Such a retinal prosthesis is described in more detail in U.S. Pat. No. 5,935,155 issued Aug. 10, 1999 for "Visual Prosthesis And Method Of Using Same," which patent is incorporated herein by reference above.

It should be noted that the retinal prosthesis 10 is merely an example, and the present invention applies to other embodiments of retinal prostheses, including retinal prostheses with different allocations of processing between external and implantable parts, and to fully implantable retinal prostheses. It should also be noted that while an example of a CCD camera was mentioned, the scope of the invention is not so limited but includes other technologies used for image acquisition equipment such as video cameras, digital cameras, CMOS cameras, etc. The present invention also may be practiced using images acquired through devices such as electromagnetic imaging (e.g., radar), or acoustic imaging (e.g., sonar), or any other device capable of generating range and angle information. It is further to be understood that the brain's ability to use information from non-intuitive sources is not well understood, and that image-like information from any source, or of any nature, wherein the image may be adjusted (or remapped) to present a more accurate spatial perception to the patient, is intended to come within the scope of the present invention. For example, data in the form of a 2 dimension representation of azimuth and range or azimuth and speed may be provided to a patient, and the adjustment of such image in intended to be included within the scope of the present invention.

Figure 2A:
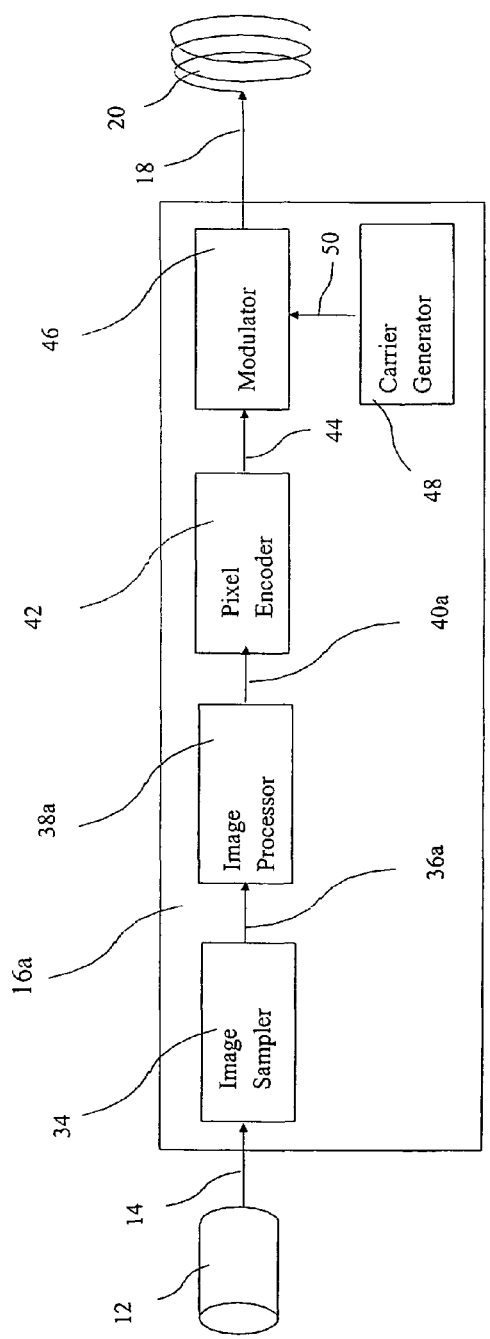
FIG. 2A shows details of an external part of the visual prosthesis wherein image sampling is performed before image processing.

A first embodiment of external electronics 16a of the retinal prosthesis 10 is illustrated in FIG. 2A. As may be observed from this figure, the video signal 14 captured by the camera 12 is output to an image sampler 34. The image sampler 34 generates a first sampled image 36a which is passed to a first image processor 38a.

The image processor 38a may perform various signal processing steps on the sampled image 36a, including the processing described by the present invention. A first processed image 40a is generated by the image processor 38a and provided to the pixel encoder 42. The processed image 40a is encoded to generate an encoded signal 44, and the encoded signal 44 is passed to a signal modulator 46. The signal modulator 46 uses the encoded signal 44 to modulate an RF carrier signal 50 generated by a carrier generator 48, to generate the RF modulated signal 18 (see FIG. 1). The modulated signal 18 is transmitted via the primary coil 20.

Figure 2B:
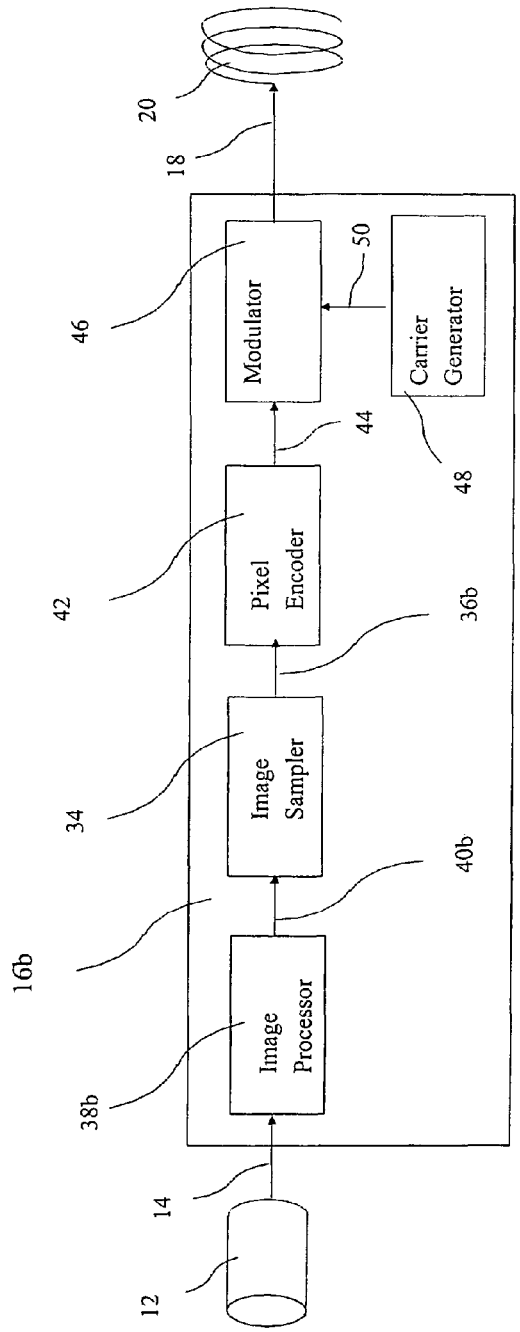
FIG. 2B shows details of an external part of the visual prosthesis wherein image sampling is performed after image processing.

A second embodiment of the external electronics 16b is shown in FIG. 2B. In this embodiment a second image processor 38b receives the video signal 14 from the camera 20. The image processor 38b generates a second processed image 40b which is provided to the image sampler 34. A second sampled image 36b is generated from the processed image 40b, which sampled image 36b is provided to the pixel encoder 42.

The basic difference between the first and second embodiments of the external electronics 16a and 16b is that the image processor 38a operates on an input which has been previously processed by the image sampler 34, which image has been down sampled (or decimated) to map onto the electrode array 32. In the second embodiment of the external electronics 16b the image processor 38b operates on the full high resolution video signal 14 before the image sampler 34 reduces the number of pixels.

Figure 3:
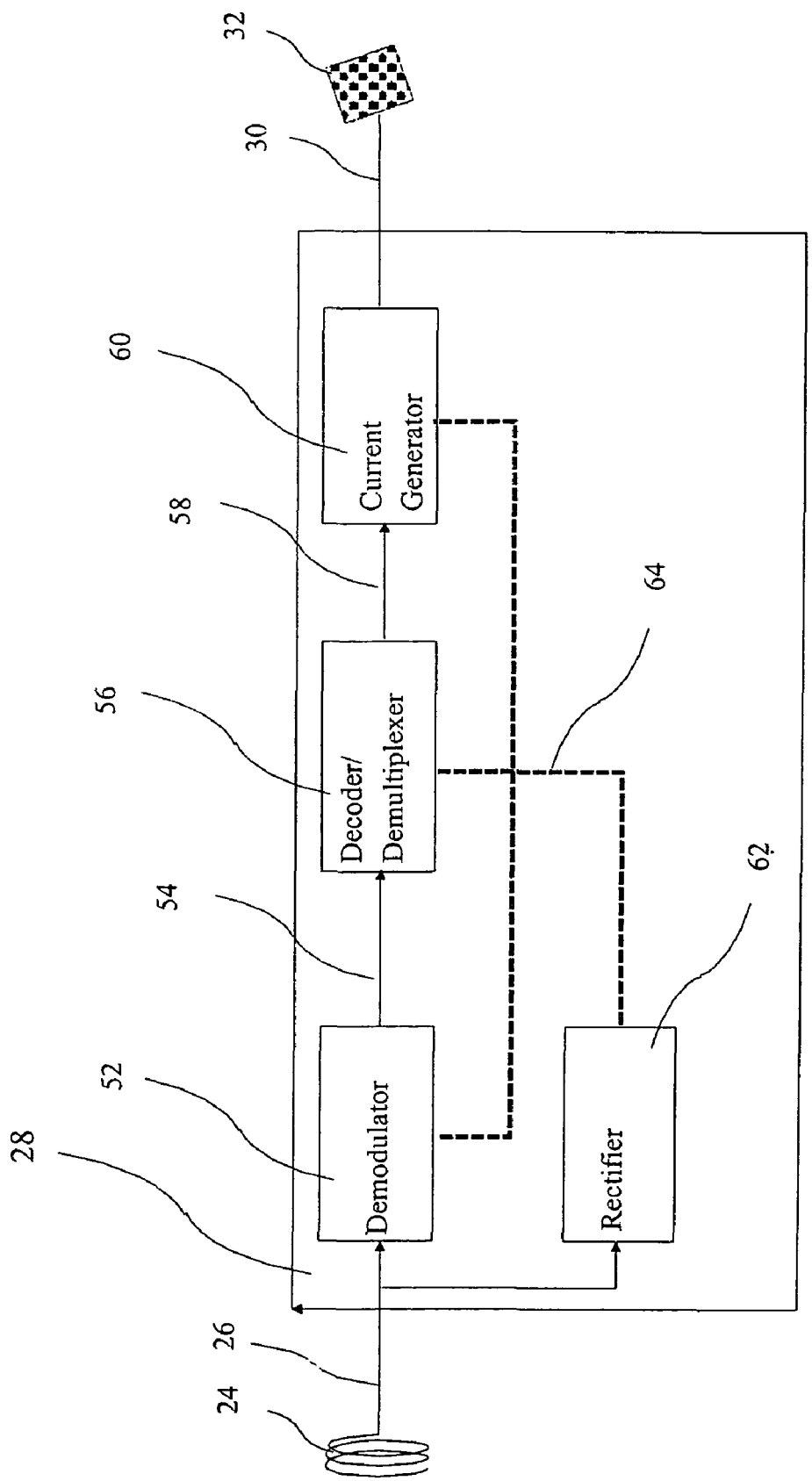
FIG. 3 shows details of an external part of the visual prosthesis wherein the image is adjusted in the camera to remove distortions.

Those skilled in the art will recognize various other steps and orders of processing that may be utilized to process the video signal 14. Any processing which processes a video signal for a retinal prosthesis, and includes the method of the present invention is intended to come within the scope of the present invention. Another embodiment of the external part of a visual prosthesis 10 is shown in FIG. 3, which embodiment includes a second camera 12a, and a third external electronics 16c. The external electronics 16c does not include an image processor 38a or 38b to adjust the image. The camera 12a includes an adjustable lens 13, and/or an adjustable CCD 15, and/or a third image processor 38c. The lens 13, CCD 15, and/or the processor 38c may be controlled to adjust a second video signal 14a carries the adjusted signal from the camera 12a to the external electronics 16c.

In a first embodiment, the lens 13 and/or the CCD 15 may be translated and/or rotated to adjust the signal 14a. In a second embodiment, the lens 13 and/or the CCD 15 may be made from a flexible, expandable material, wherein the lens 13 and/or the CCD 15 may be mechanically manipulated to alter the shapes of the lens 13 and/or the CCD 15. Additionally, the first and second embodiments may be combined to provide greater adjustment of the signal 14a. The processor 38c may be used independently, or in conjunction with the lens 13 and/or the CCD 15 to adjust the signal 14a, or the processor 38c may be omitted from the camera 12a. The camera 12a may also be used with the external electronics 16 or 16b.

In another example, a corrective lens may be provided that has been ground to compensate for distortions perceived by the patient. Also, the camera 12 or 12a may be physically rotated to adjust the image perceived by the patient.

An example of the implantable electronics 28 is shown in FIG. 4A. The received signal 26 received by the secondary coil 24 is provided to a demodulator 52, and to a rectifier 62. The rectifier 62 processes the received signal 26 to generate a DC power signal used to power the implantable device. The rectifier 62 may be a half wave or full wave rectifier. The demodulator 52 filters the received signal 26 to recover a demodulated signal 54 which is substantially like the encoded signal 44 (i.e., contains the same information that the signal 44 carried). The demodulated signal 54 is provided to a decoder/demultiplexer 56 which processes the demodulated signal 54 to generate a stimulation control signal 58. The stimulation control signal 58 is processed by the current generator 60 to generate the stimulation current signal 30 which is used by the electrode array 32 to stimulate the retina.

Figure 4:
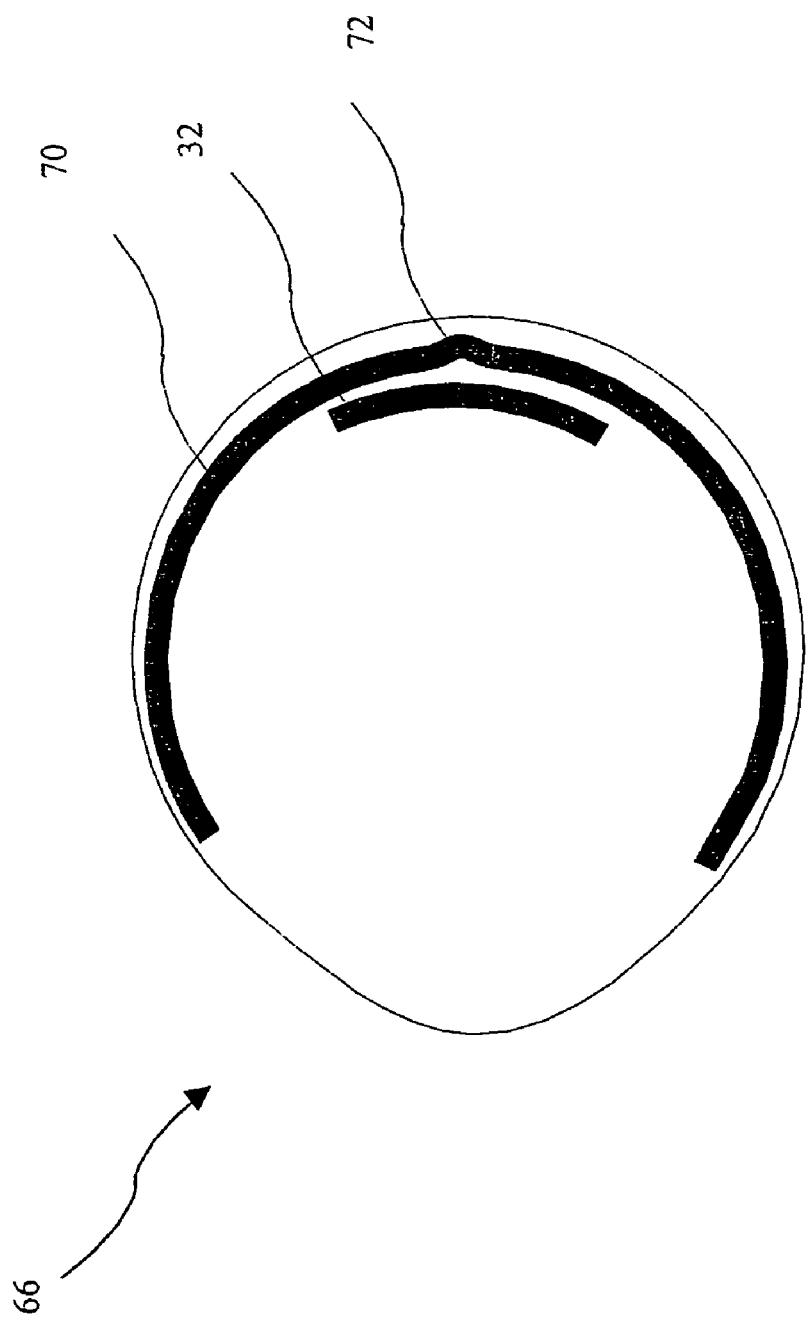
FIG. 4 shows details of an implantable part of the visual prosthesis.
Figure 5A:
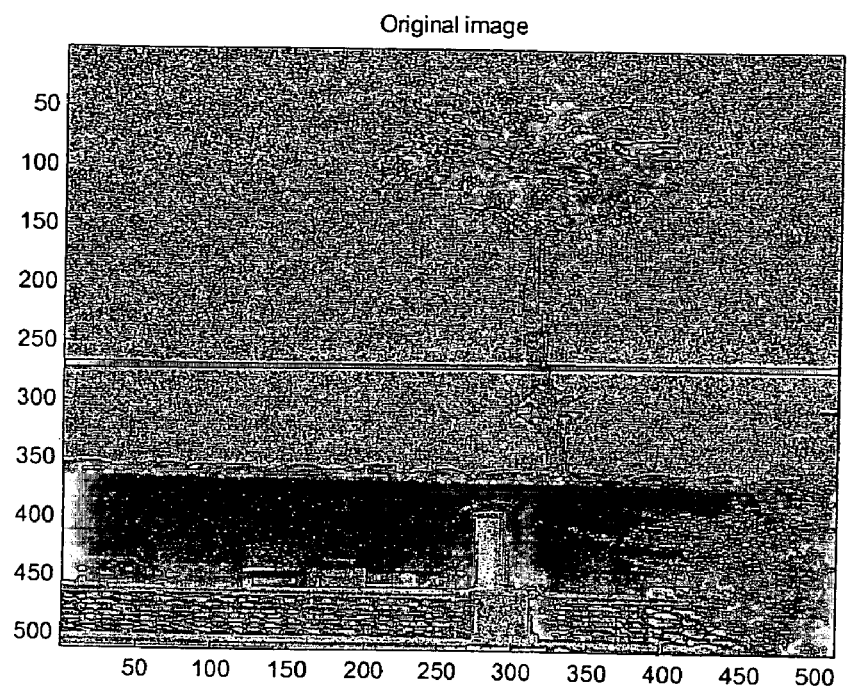
FIG. 5 depicts an electrode array of the visual prosthesis residing over the retina.
Figure 5B:
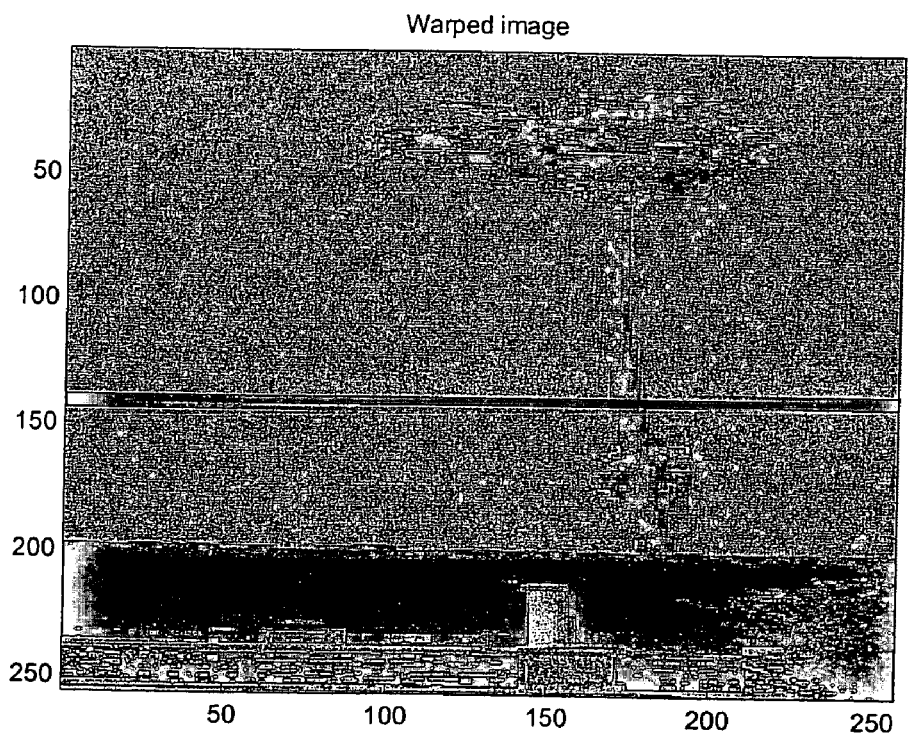
Figure 5C:
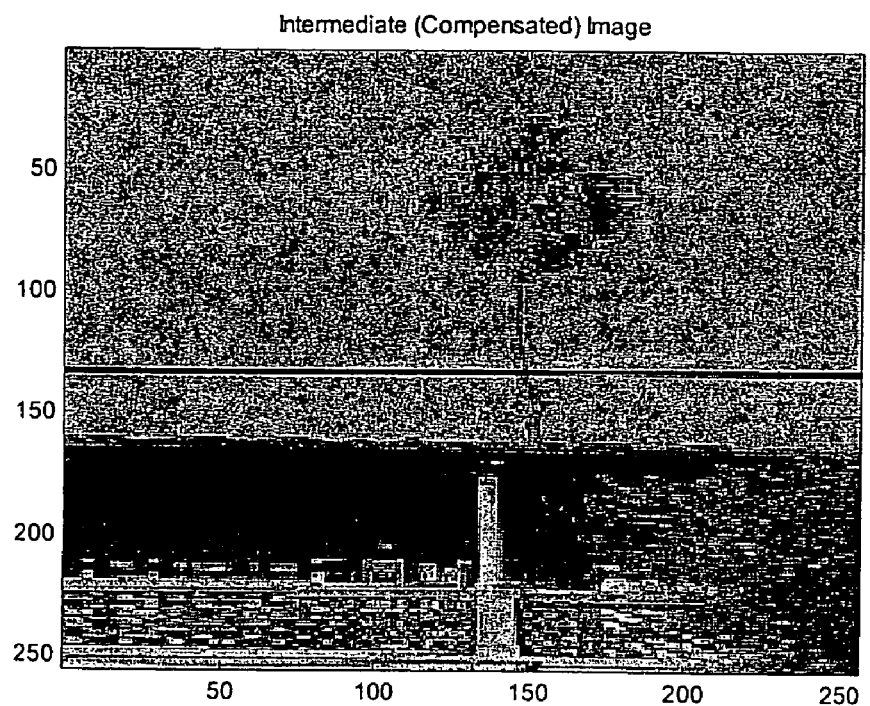
Figure 5D:
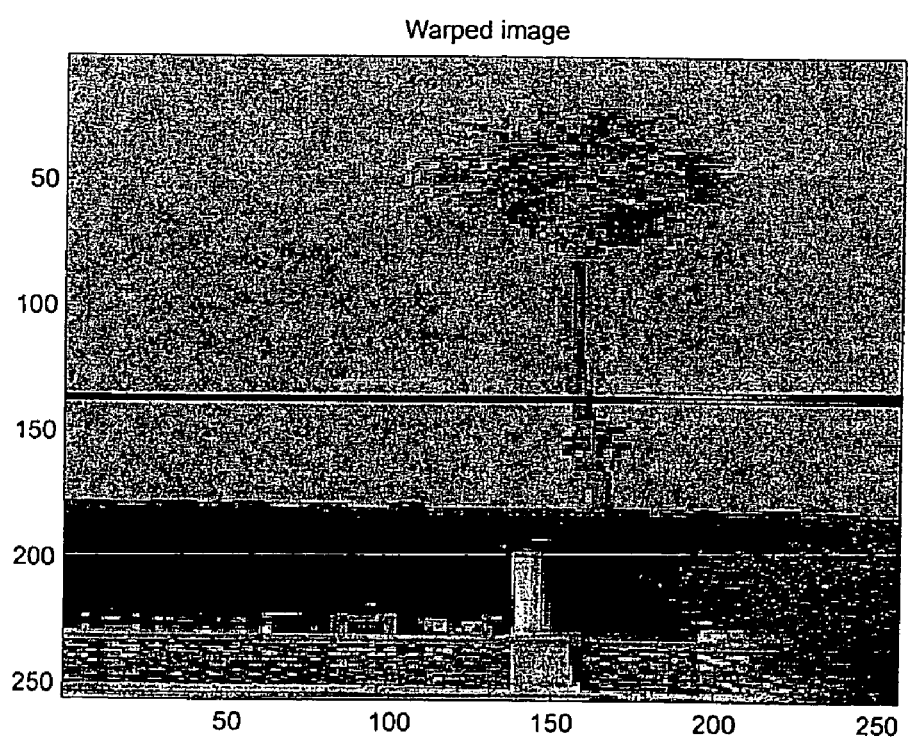

The example presented in FIG. 4 is one of many embodiments of implantable electronics. Any circuit which receives a transmitted signal and generates stimulation current for retinal stimulation is intended to come within the scope of the present invention. The details of such implanted circuit is not important to the present invention, and merely provides a conduit for an externally generated signal to result in retinal stimulation.

The implantable electronics may also include a signal processor, for adjusting an image perceived by the patient to reduce or eliminate distortions. A fourth image processor 38d processes the stimulation control signal 58 to generate a third processed image 40c. In another embodiment, a single implantable electronics may perform the processing described in FIGS. 2A, 2B, and/or 3, and the processing described in FIG. 4.

The processing performed in the implantable processor 28 may be combined with the processing performed in the external processor 16 to obtain a fully implantable visual prosthesis. Such combination may be into a single implantable device, or into two or more cooperating implantable devices. Also, the image processing performed in the image processor 38a, 38b, or 38c may be performed in the implantable electronics 28.

The electrode array 32 is implanted on the retina 70 of the eye 66, as shown in FIG. 5. The greatest concentration of nerves of the retina 70 is in the area of the macula 72, and the sensation of vision in similarly centered corresponding to the macula 72. Preferably, the electrode array 32 is centered over the macula 72, but in practice, there may be both translational and rotational misalignments of the electrode array 32 with the macula 72. These misalignments may result in a perception of the image being shifted vertically or horizontally, and/or being rotated.

Additionally, the spatial perception of the patient may vary with corresponding to different parts of the retina. As a result, an object may be warped, and the perceived ratio of width to height may not reflect the actual ratio. As a result of the false perception of an objects relative dimensions, the object may not be recognized by the patient.

An example of an original image is shown in FIG. 6A. The image presents several features including a tree, a man climbing the tree, and a pillar. The same image is presented in FIG. 6B as the image may be perceived by a patient. The image perceived by a patient includes undesirable characteristics (i.e, distortions). For example, the top of the tree, the man in the tree, and the pillar are wider in FIG. 6B than in FIG. 6A. Such distortion may result from the way the brain processes information from different areas of the retina, especially the border between the macula and the periphery around the macula, or of translations or rotations of the electrode array 32 when it is implanted.

The present invention reduces or eliminates such distortion, and other distortions, by adjusting the image so that the perceived image will more accurately reflect the original image. Such adjustment may be performed in the external electronics 16a or 16b (FIG, 2A, 2B), in the camera 12a (FIG. 3), or in the implantable electronics 28. An example of how the image may be adjusted by image processing is shown in FIG. 6C. The processing performed in the image processor basically is the inverse of the distortion perceived by the patient. The unprocessed image widened the tree, the man, and the pillar. The processing done in the image processor narrows the tree, the man, and the pillar.

The resulting image perceived by the patient in shown in FIG. 6D. Although some granularity is present due to the number of electrodes being fewer than the pixels of the original image, the image now presents the tree, the man, and the pillar with proportions very close to the original image. The method of the present invention used to reduce the distortion is described in the following paragraphs.

In a first embodiment of a method according to the present invention, an array of symbols may be presented to the patient. An obvious selection of symbols is a set of array indices corresponding to the position of each symbol. An example of an original image is shown in FIG. 7A of an eight by eight array using such indices. An example of how the original image may be distorted is shown in FIG. 7B, wherein the top left corner of the image has been pushed down and to the right, and the bottom left corner of the image has been pushed to the right, and up.

The patient is provided with the knowledge that the image should be a rectangular (in this example square) array of indices. Based on the knowledge of how the image should look, the use may either directly manipulate the image, or direct a clinician to manipulate the image, to reduce or eliminate the distortion. For example, the patient might be given a joy-stick, mouse, or some other input device to manipulate the image. The patient may select a corner to manipulate by motion of the joy-stick, or tell the clinician which corner the patient intends to manipulate. The patient may then move the joy stick to "stretch" the perceived image to obtain the intended perceived image. The patient may proceed to spatially adjust each corner perceived to be distorted. Alternatively, the patient may direct the clinician to manipulate the image to reduce or eliminate the distortion. Advantageously, the use of an image of array indices allows the patient to indicate which part of the image a spatial adjustment is directed to.

An intermediate image representing the spatial adjustment performed by the image processor 38a, 38b, or 38c or the camera 12a, and the processed image 40a, 40b, or 40c (or in the case of the camera 12a, the video signal 14a). The intermediate image reflects the inverse of the distortion shown in FIG. 7B. When the processed image is presented to the patient, the patient now perceives an image with the distortion reduced or eliminated.

Figure 7B:
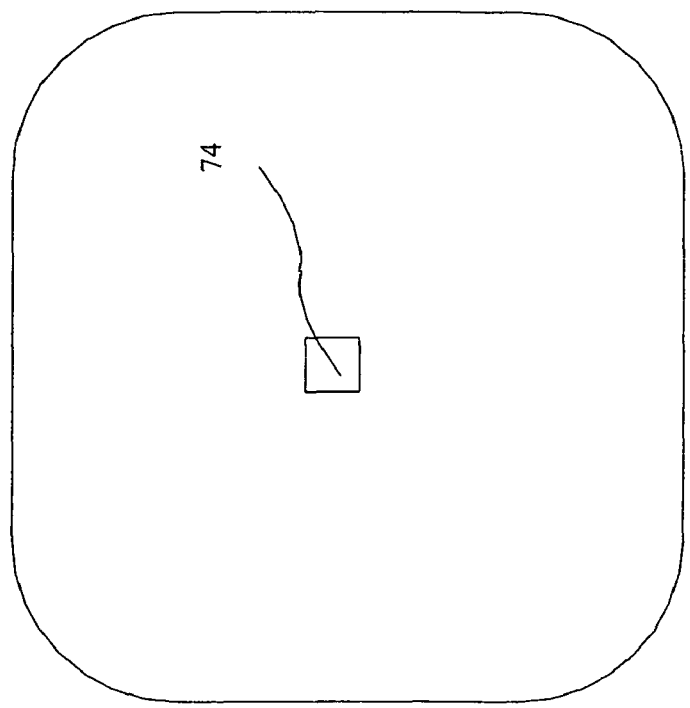
FIG. 7B shows a distorted version image of FIG. 7A.
Figure 7A:
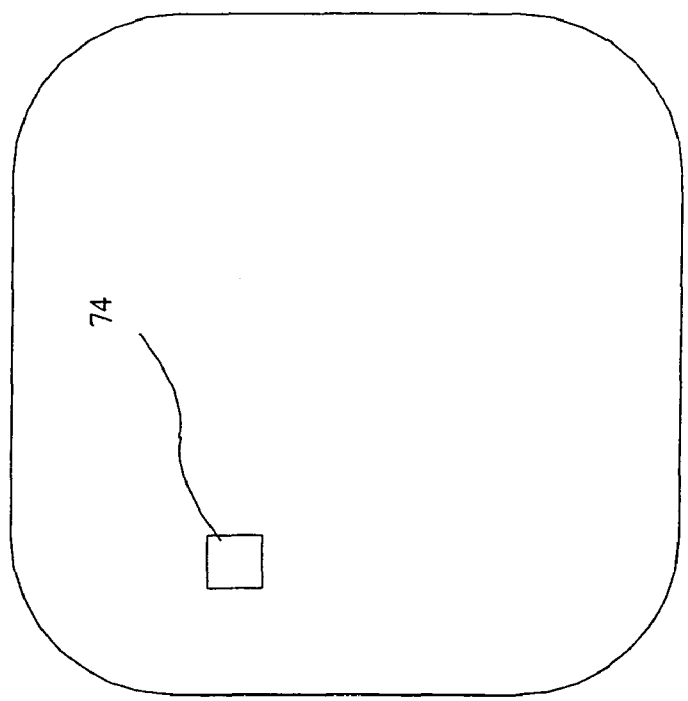
FIG. 7A shows an original image of an 8×8 array of symbols (in this case the symbols are the indices of the position of each symbol)

Those skilled in the art will recognize that variations of the method described in FIGS. 7A-7B may also be exercised. For example, the total image space perceived by the patient may be dived into 2 or more sections, and the method of FIGS. 7A-7B may be applied independently to each section. The patient may also use a joy-stick, or other input device to select a portion of the total perceived image to adjust. These and other variations to the method described herein are intended to come within the scope of the present invention. In cases where the patient may only perceive coarse images, symbols such as circles, squares, stars, and the like, may be substituted for the indices in FIGS. 7A-7B.

Figure 8B:
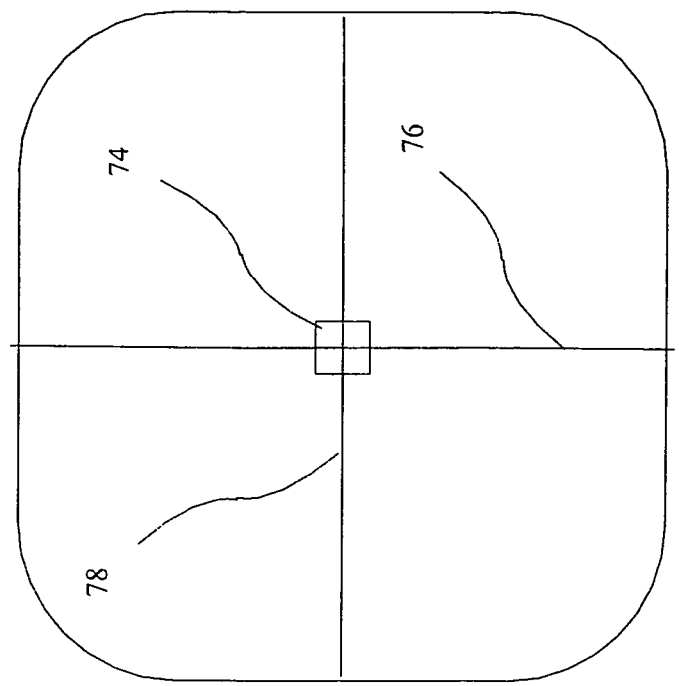
FIG. 8B depicts the centering feature of FIG. 8A after the image has been adjusted by the image processor to remove the distortion.
Figure 8A:
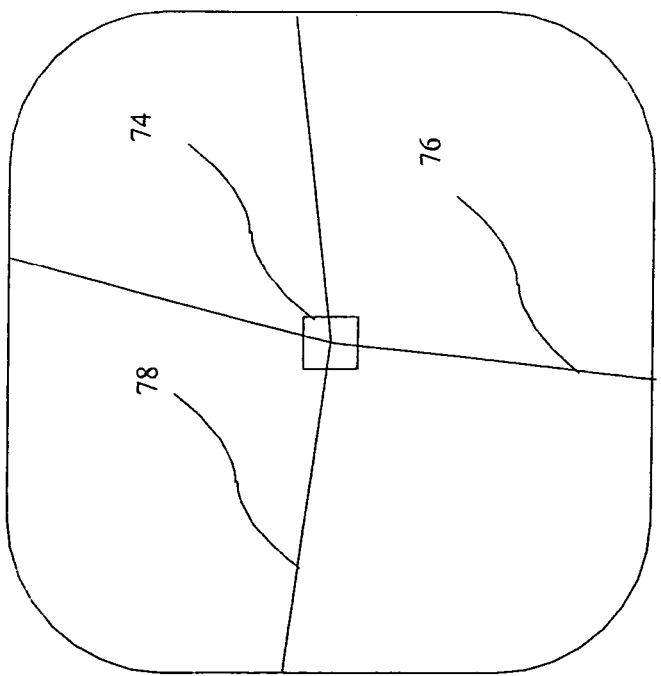
FIG. 8A shows a perceived image including a centering feature, wherein the perceived image shows a distortion of the feature.
Figure 11B:
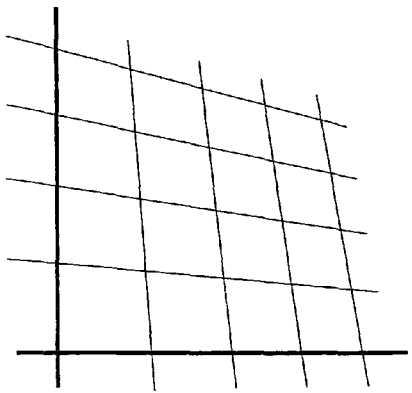
FIG. 11B depicts an example of how the image of FIG. 11A might be perceived by a patient (the top of the image, corresponding to the first line, and left side of the image, corresponding to the second line, remain substantially horizontal and vertical)
Figure 11D:
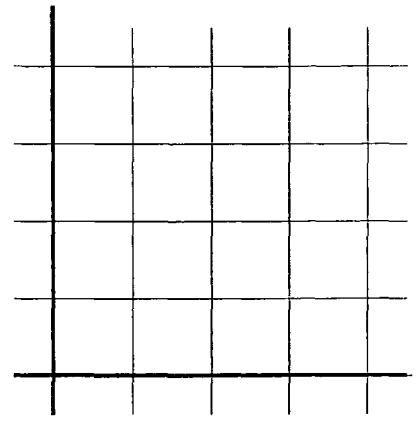
FIG. 11D depicts the image perceived by the patient from stimulation based on the adjusted image of FIG. 11C.
Figure 11A:
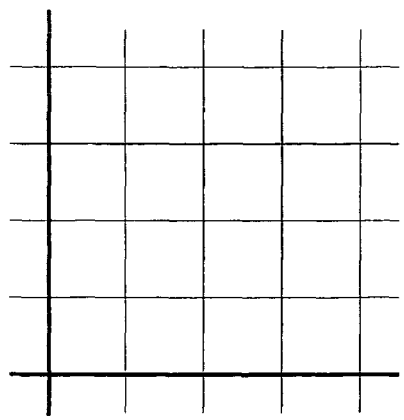
FIG. 11A shows a lower right quadrant of an original image, which original image has been centered, and which original image has been adjusted to make the first line substantially horizontal and the second line substantially vertical.
Figure 11C:
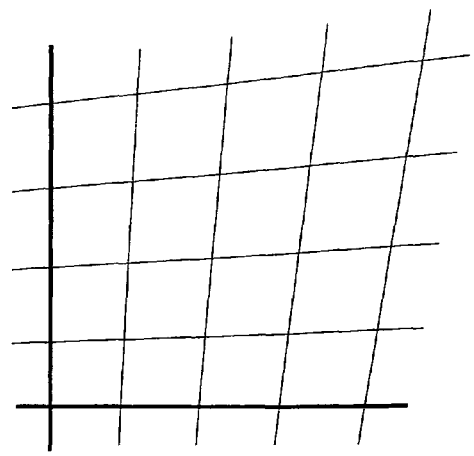
FIG. 11C depicts an adjusted image generated by the image processor (i.e., at the output of the image processor) to compensate for the distortion perceived by the patient in the image of FIG. 11B.

A second method for adjusting an image to reduce or eliminate distortion is now described. An image is provided with a defined feature, which feature is intended to be perceived by the patient as being directly ahead of the patient. An example of a square centering feature 74 is shown in FIG. 8A. Both the size and shape of the feature may vary, and some feature sizes and shapes may be preferred by some patients, while other feature sizes and shapes may be preferred by other patients. The patient may either directly manipulate the image, as described in FIGS. 7A-7B, or direct a clinician to manipulate the image, to adjust the perceived location of the feature 74 to be directly ahead of the patient. As a result of this adjustment, any translation of the center of the image is reduced or eliminated as shown in FIG. 8B.

Another method for reducing or eliminating distortion is to align boundaries within the image. An image with misaligned boundaries is shown in FIGS. 9A and 9B. In this example, the image has been centered as described in FIGS. 8A and 8B, however the method described in FIGS. 9A and 9B may be performed on an image that has not been centered. Such centering is not required for the alignment of boundaries, but may provide better results. The original boundaries are a vertical line 76 passing through the center of the image, and a horizontal line 78 passing through the center of the image. Other lines, for example an "X" may also be used, and different numbers of lines or patterns of lines 76 and 78 may be preferred by different patients. The patient may adjust the end points only of the lines 76 and 78, or may adjust points along the lines 76 and 78. In extreme cases, the misaligned lines 76 and 78 may be severely arced, and in these cases it may be necessary to make adjustments at several points along the lines 76 and 78 to align the boundaries. An example of adjusted lines 76 and 78 are shown in FIG. 9B. The lines 76 and 78 maybe adjusted directly by the patient, or by the clinician guided by the patient.

In cases where the patient merely manipulates the ends of the lines 76 and 78, each point along the lines 76 and 78 may be proportionally adjusted. If the patient manipulates several points along the lines 76 and 78 to align the lines 76 and 78, various known methods may be automatically applied to points between the manipulated points. For example, a least squares curve fit, a spline fit may be applied, or the like may be applied to adjust intermediate points. Such methods are well known in the mathematical arts.

Another method for reducing or eliminating distortion from the perceived image is to break the image into sub-images as shown in FIGS. 10A-10D. The processing described for the sub-images may be performed after the processing described in FIGS. 9A and 9B, or may be performed independently. After the processing described in FIGS. 9A and 9B has been exercised, the sub-images may be defined by the lines 76 and 78 which were adjusted. An example wherein the sub-images are 4 quadrants of the original image is shown in an un-distorted view in FIG. 10A. The same four quadrants are shown in a distorted view as perceived by the patient in FIG. 10B. The advantage of using pre-adjusted (as described in FIGS. 9A and 9B) is apparent in that the joint boundaries of the quadrants fall on the lines 76 and 78, which lines were previously adjusted to reduce or eliminate distortion, and therefore, these sides of the quadrants are not substantially distorted. The patient is thus left with a more manageable task than if all of the sides of the sub-images were distorted.

The quadrants may be more easily identified for the patient by first illuminating corner markers at the corners of each quadrant. The patient can align these corner markers to a known reference. The markers can be used to align the quadrant relationships to other quadrants and to help the patient identify the periphery of each quadrant.

In the example of FIG. 10B the patient may directly adjust the corners adjacent to the image center, and opposite the image center, or the patient may direct the clinician to adjust the image. Because the common corner and sides have already been adjusted, they will not be altered, and advantageously, gaps or overlaps between quadrants will not be created. When a corner of a quadrant is adjusted, every point within the quadrant may be consistently adjusted using two-dimensional linear interpolation.

As described in FIG. 6C, the adjustment of the image results in the creation of an inverse to the distortion, which inverse is crated in the image processors 38A and 38B. The processed image 40a, 40b, or 40c reflects this inverse as shown in FIG. 10C. When this inverse processing is performed, the distortion in the perceived image will be reduced or eliminated as shown in FIG. 10D.

Those skilled in the art will recognize that the quadrants may be presented to the patient by images other than the outlines shown in FIGS. 10A-10D. An example using dots is shown in FIGS. 11A-11D. In these additional examples, only the lower right quadrant is shown. Those skilled in the art will recognize that patients may prefer other patterns, and the exercise of the method described herein using any other pattern is intended to come within the scope of the present invention.

The adjustments described in FIGS. 7A-11D were spatial adjustments. Other non-spatial adjustments to the image provided to the patient may be made to aid the patient in interpreting the image. For example, some images may be more recognizable by the patient if a black/white inversion of the image is performed. An image inversion may also reduce the power requirements. For example, black lettering on a white page will require most electrodes (white paper) to operate at high power while a few electrodes (black letters) operate at low power. Inverting the signal to yield white lettering on a black page will significantly reduce power consumption. Black/white image inversion may be performed by linearly mapping image intensity from a range between zero and one into a range between one and zero. Such non-spatial adjustments may be performed in the camera (or any other image source), in the external electronics 16a, 16b, or 16c, preferably in the image processor 38a, 38b, or 38c, or in the internal electronics 28a or 28b.

A method according to the present invention, in the most general form, is described in FIG. 13A. The method comprises determining distortions in an image adapted to be presented to a patient through a visual prosthesis, and adjusting the visual prosthesis (i.e., the method and/or apparatus comprising the visual prosthesis) used to provide the image to reduce or eliminate the distortions.

One embodiment of the method described in FIG. 13A is shown in FIG. 13B. In the embodiment of the method described in FIG. 13B, the distortions are determined by providing an image (i.e., providing visual stimulation to the patient using a visual prosthesis) to the patient, and determining the perceived distortions from the patient's perception of the image. In another embodiment of the method described in FIG. 13A is shown in FIG. 13C. In the embodiment shown in FIG. 13C, the distortions are determined by observing objective indications indicative of distortions. For example, a clinician may observe the topology of the patient's eye, the final placement of the electrode array, consider past observations (i.e., experience), or any other observation not requiring feedback from the patient. The methods of FIGS. 13B and 13C may also be combined to determine the distortion based on a combination of the patients subjective perception of the images, and the clinician's objective observations.

The method described in FIG. 13B may be exercised as shown in FIG. 14A by providing a scene to the patient. This method may provide the best results for a high resolution visual prosthesis and a patient who has recently lost their sight. The method described in FIG. 13B may be exercised as shown in FIG. 14B by providing an image adapted to facilitate image adjustment to the patient. Such image may be similar to the images described in FIGS. 7-12, or some other figures.

In another embodiment of the method of the present invention, the electrode array 32 may be adjusted during the implant procedure to remove distortions due to the position of the electrode array 32 on the retina 70. One embodiment of a method is shown in FIG. 14C, the method comprising: providing an image comprising a scene to the patient; determining the perceived distortions in the scene (i.e., translations and rotations of the scene as perceived by the patient); and adjusting the electrode array 32 to remove the distortions. The method described in FIG. 14C may be exercised repetitively as many times as necessary to obtain good results.

Another method similar to the method described in FIG. 14C is shown in FIG. 14D, wherein an image adapted to facilitate electrode array 32 adjustment is provided to the patient in place of a scene.

The method described in FIG. 14B may further be exercised as shown in FIGS. 15A-15C. A method for providing a centering feature to aid the patient in centering the perceived image is shown in FIG. 15A. A method for providing an image including at least one boundary to aid the patient in creating boundaries between sub-images is shown in FIG. 15B. A method for providing sub-images to aid the patient in independently adjusting portions of the entire image is shown in FIG. 15C.

A method for adjusting the image perceived by the patient based on observations by a clinician is shown in FIG. 16A. The method comprises: observing the position of the electrode array 32 on the patient's retina 70 (see FIG. 5) to determine if the electrode array 32 is translated away from the intended position of the electrode array 32 on the retina 70; translating the image to compensate for any translations of the electrode array 32 with respect to the retina 70; rotating the image to compensate for any rotation of the electrode array 32 with respect to the intended rotation (i.e., angle) of the electrode array 32 with respect to the retina 70; and adjusting (e.g., de-warping) the image to compensate for known distortions relative to the position of the electrode array 32 with respect to the retina 70. For example, known distortions may be determined for individual patients prior to implanting the electrode array.

Another method for adjusting the image perceived by the patient is shown in FIG. 16B, comprising: observing the topology of the patient's retina; and adjusting the image to compensate for the observed topology.

A first embodiment of a method for providing an adjusted image to a patient is described in FIG. 17A, the method comprising: obtaining an image; sampling the image; processing the sampled image to reduce or eliminate distortion in the image; encoding the processed image; generating a carrier signal; modulating the carrier signal with the encoded signal; transmitting the modulated signal to the implantable electronics 28; receiving the transmitted signal in the implantable electronics 28; processing the received signal to generate a stimulation signal; and stimulating the patient's retina with the stimulation signal.

Another embodiment of a method for providing an adjusted image to a patient is described in FIG. 17B, the method comprising: obtaining an image; processing the image to reduce or eliminate distortion in the image; sampling the processed image; encoding the processed image; generating a carrier signal; modulating the carrier signal with the encoded signal; transmitting the modulated signal to the implantable electronics 28; receiving the transmitted signal in the implantable electronics 28; processing the received signal to generate a stimulation signal; and stimulating the patient's retina with the stimulation signal.

Yet another embodiment of a method for providing an adjusted image to a patient is described in FIG. 17C, the method comprising: obtaining an image; processing the image to generate a pixel encoded signal; modulating the carrier signal with the encoded signal; transmitting the modulated signal to the implantable electronics 28; receiving the modulated signal in the implantable electronics 28; recovering the pixel encoded signal; processing the encoded signal to generate a reduced distortion stimulation signal; and stimulating the patient's retina with the stimulation signal.

The methods described in FIGS. 17A-17C for adjusting an image included processing an existing image. A method including adjusting an image within a camera is described in FIG. 18A, wherein the method comprises: obtaining an image using a lens adapted to reduce or eliminate distortion; processing the image to generate a pixel encoded signal; modulating a carrier signal with the pixel encoded signal; transmitting the modulated signal; receiving the transmitted signal; processing the received signal to generate a stimulation signal; and providing the stimulation signal to the retina.

A second method including adjusting an image within a camera is described in FIG. 18B, wherein the method comprises: obtaining an image using a CCD adapted to reduce or eliminate distortion; processing the image to generate a pixel encoded signal; modulating a carrier signal with the pixel encoded signal; transmitting the modulated signal; receiving the transmitted signal; processing the received signal to generate a stimulation signal; and providing the stimulation signal to the retina.

A third method including adjusting an image within a camera is described in FIG. 18C, wherein the method comprises: obtaining an image; processing the image within the camera to generate an adjusted video image; processing the image to generate a pixel encoded signal; modulating a carrier signal with the pixel encoded signal; transmitting the modulated signal; receiving the transmitted signal; processing the received signal to generate a stimulation signal; and providing the stimulation signal to the retina.

Accordingly, what has been shown is a method and apparatus for the adjustment of a distorted image, which method and apparatus is of particular utility with an implantable medical device, e.g., a retinal prosthesis, for reducing image distortions. While the invention has been described by means of specific embodiments and applications thereof, it is understood that numerous modifications and variations could be made thereto by those skilled in the art without departing from the spirit and scope of the invention. For example, while the invention has been specifically described for use in processing a high resolution video signal to drive a retinal (or cortical) prosthesis, it is believed that such processing will additionally provide benefit when the low resolution output device is a video output display, e.g., LCD display, that has a lower resolution than the video input signal.

Additionally, the description and the illustrated input pixel arrays and subsets have been square in shape, i.e., with symmetrical aspect ratios, which correspond to a similar square aspect ratio for the output pixel array. However, the aspect ratios of the input and output pixel arrays need not be the same. Accordingly, embodiments where the input pixel data is processed, e.g., formed into subsets by the video processor, to compensate for the difference in these aspects ratios are considered to be within the scope of the present invention. Additionally, embodiments of the present invention may use subsets that are square, rectangular, circular, oval, non-overlapping or overlapping. Furthermore, while the previous description was generally directed toward the use of transformation filters that operated on the pixel subsets, embodiments that use transformation filters to process the input video prior to subsetting are also considered to be within the scope of the present invention.

It is therefore to be understood that within the scope of the claims, the invention may be practiced otherwise than as specifically described herein.

What is claimed is:

1. A method for providing artificial sight to a patient, comprising:
generating an original image;
processing the original image to generate a processed image;
generating a first stimulation current based on the processed image;
providing a first stimulation to a retina of the patient using the first stimulation current;
perceiving a first perceived image produced by the first stimulation, wherein the first perceived image is a spatially distorted image of said original image,
determining a spatial distortion between the original image and the first perceived image;
generating a second stimulation current;
providing a second stimulation to the retina of the patient using the second stimulation current; and
perceiving a second perceived image produced by the second stimulation the second perceived image being representative of said original image,
wherein spatial distortion of the second perceived image is lower than spatial distortion of said first perceived image and wherein a stimulation difference between said first stimulation and said second stimulation corresponds to an adjustment of the determined spatial distortion.

2. The method of claim 1 wherein the adjustment of the determined spatial distortion of the first perceived image includes adjusting a position of at least one centering feature.

3. The method of claim 1 wherein the adjustment of the determined spatial distortion of the first perceived image includes adjusting a position of a feature directly ahead.

4. The method of claim 1 wherein the adjustment of the determined spatial distortion of the first perceived image includes adjusting a first line to be substantially horizontal and adjusting a second line to be substantially vertical.

5. The method of claim 1 wherein the adjustment of the determined spatial distortion of the first perceived image quadrants of the image to obtain a desired pattern.

6. The method of claim 1 wherein the adjustment of the determined spatial distortion of the first perceived image includes using an image source adapted to adjust the first perceived image to remove spatial distortions.

7. The method of claim 6 wherein the adjustment of the determined spatial distortion of the first perceived image includes using an image source including an adjustable lens adapted to remove spatial distortions.

8. The method of claim 6 wherein the adjustment of the determined spatial distortion of the first perceived image includes using an image source including an adjustable CCD adapted to remove distortions.

9. The method of claim 6 wherein the adjustment of the determined spatial distortion of the first perceived image includes using an image source including an image processor adapted to remove spatial distortions.

10. The method of claim 6 wherein the adjustment of the determined spatial distortion of the first perceived image includes using an image source including a corrective lens adapted to remove spatial distortions.

11. The method of claim 1 wherein the adjustment of the determined spatial distortion of the first perceived image includes spatially adjusting a stimulating electrode.

12. The method of claim 1, further comprising providing the patient with information on a desired appearance of the original image.

13. The method of claim 12, wherein the first image is spatially adjusted based on the patient's subjective perception of the difference between the first perceived image and the desired appearance of the original image to obtain the second perceived image.

14. The method of claim 1, wherein the adjustment includes an alignment of boundaries of said first perceived image with respect to boundaries of the original image.

15. The method of claim 1, wherein the original image and the first perceived image are divided in sub-images by way of respective lines, and wherein said stimulation difference corresponds to an alignment of at least one of the lines of said first perceived image with respect to at least one of the lines of said original image.

* * * * *